United States Patent
Takenaka et al.

(10) Patent No.: US 6,916,614 B1
(45) Date of Patent: Jul. 12, 2005

(54) GENE DETECTING CHIP, DETECTOR, AND DETECTING METHOD

(75) Inventors: Shigeori Takenaka, Koga (JP); Kazuhiko Uchida, Tsukuba (JP); Takatoshi Miyahara, Chiba (JP)

(73) Assignee: TUM Gene, Inc., Chiba (JP)

(*) Notice: Subject to any disclaimer, the term of this patent is extended or adjusted under 35 U.S.C. 154(b) by 443 days.

(21) Appl. No.: 09/868,576

(22) PCT Filed: Oct. 20, 2000

(86) PCT No.: PCT/JP00/07342
§ 371 (c)(1), (2), (4) Date: Mar. 8, 2002

(87) PCT Pub. No.: WO01/29550
PCT Pub. Date: Apr. 26, 2001

(30) Foreign Application Priority Data

Oct. 20, 1999 (JP) .......................... 11-298917

(51) Int. Cl.[7] .............................................. C12Q 1/68
(52) U.S. Cl. ........................... 435/6; 435/7.1; 435/91.1; 435/91.2; 435/287.2; 435/288.3; 204/403.01
(58) Field of Search ..................... 204/403.01; 435/6, 435/7.1, 91.1, 91.2, 287.2, 288.3

(56) References Cited

U.S. PATENT DOCUMENTS

| | | |
|---|---|---|
| 4,343,684 A | 8/1982 | Lechtzen |
| 4,840,893 A | 6/1989 | Hill et al. |
| 4,857,831 A | 8/1989 | Davies et al. |
| 5,108,576 A | 4/1992 | Malmros et al. |
| 5,614,004 A | 3/1997 | Wachi et al. |
| 5,814,450 A | 9/1998 | Stanley et al. |
| 5,866,321 A | 2/1999 | Matsue et al. |
| 5,873,992 A | 2/1999 | Glezen et al. |
| 6,048,692 A * | 4/2000 | Maracas et al. ............... 435/6 |
| 6,071,394 A | 6/2000 | Cheng et al. |
| 6,093,370 A | 7/2000 | Yasuda et al. |
| 6,126,800 A | 10/2000 | Caillat et al. |
| 6,274,373 B1 | 8/2001 | Virtanen |
| 6,340,568 B2 * | 1/2002 | Hefti ............................. 435/6 |
| 6,368,851 B1 * | 4/2002 | Baumann et al. ........ 435/285.2 |
| 6,749,731 B2 | 6/2004 | Kobori et al. |

FOREIGN PATENT DOCUMENTS

| | | |
|---|---|---|
| EP | 0 882 981 A1 | 12/1998 |
| JP | 56-152958 A | 11/1981 |
| JP | 9-288080 | 11/1997 |
| JP | 09-288085 | 11/1997 |

OTHER PUBLICATIONS

Bain, C. D. et al., "Formation of Monolayer Films by the Spontaneous Assembly of Organic Thiols from Solution onto Gold," J. Am. Chem. Soc., 111: 321–335 (1989).

(Continued)

Primary Examiner—David A. Redding
(74) Attorney, Agent, or Firm—Covington & Burling

(57) ABSTRACT

A detecting chip (2) comprising a body (5) and a frame (4) both detachable from each other. A large number of projecting pin electrodes (10) are arranged in a matrix inside the body (5). Oligonucleotide consisting of different gene sequences is fixed to the pin electrode (10). A common electrode is so disposed in a recess (8) in a frame (4) as to be out of contact with the pin electrodes (10). A DNA sample is placed in the recess (8). By applying a voltage between the common electrode and the pin electrodes (10), a current is detected to detect a hybridized two-strand DNA, thus analyzing a gene DNA.

28 Claims, 8 Drawing Sheets

OTHER PUBLICATIONS

Gooding, J. J. et al., "Platinum–Catalyzed Enzyme Electrodes Immobilized on Gold Using Self–Assembled Layers," Anal. Chem, 70: 2396–2402 (1998).

Downs, Mark, et al., "New DNA Technology and the DNA Biosensor," Analytical Letters, vol. 20 (12), pp. 1897–1927 (1987).

Hashimoto, Koji, et al., "DNA sensor for electrochemical gene detection," Preparing for Clinical Care Analyses in the 21st Century, 16th International Symposium, 1996.

Molinier–Jumel, Catherine, et al., "Electrochemical Study of DNA–Anthracyclines Interaction," Biochemical and Biophysical Research Communications, vol. 84, No. 2, pp. 441–449 (1978).

Palecek, Emil, "Adsorptive Transfer Stripping Voltammetry: Determination of Nanogram Quantities of DNA Immobilized at the Electrode Surface," Analytical Biochemistry vol. 170, pp. 421–431 (1988).

Takenaka, Shigeori, et al., "Bis–9–acridinyl Derivative Containing a Viologen Linker Chain: Electrochemically Active Intercalator for Reversible Labelling of DNA," J. Chem. Soc., Chem. Commun., vol. 21, pp. 1485–1487 (1990).

Takenaka, Shigeori, et al., "DNA Sensing on a DNA Probe–Modified Electrode Using Ferrocenylnaphthalene Diimide as the Electrochemically Active Ligand," Anal. Chem. vol. 72, pp. 1334–1341 (2000).

Takenaka, Shigeori, et al., "Electrochemically active threading intercalator with high stranded DNA selectivity," J. Chem. Soc., Chem. Commun., No. 10, pp. 1111–1112 (1998).

Takenaka, Shigeori, "Synthetic threading intercalators as a new analytical probe for nucleic acid and gene detection," Business Kagaku, vol. 48, No. 12, pp. 1095–1105 (1999).

Takenaka, Shigeori, et al., "Threading Intercalators as a New DNA Structural Probe," Bull. Chem. Soc. Jpn, vol. 72, pp. 327–337 (1999).

Yamashita, Kenichi, et al., "Electrochemical Detection of Base Pair Mutation," Chemistry Letters, pp. 1038–1039 (2000).

Ihara, Toshihiro et al., "Synthesizing and Applying the Bis–Inercalator as an Electrochemical Detection Probe of DNA," Proceedings of the Japan Society for Analytical Chemistry, p. 54 (1989).

Takanaga, Shigeori et al., "Synthesizing the Electrochemical Threading Type Intercalator and Applying the Electrochemical Threading Type Intercalator to a DNA Sensor," Proceedings of the Japan Society for Analytical Chemistry, pp. 137–138 (1996).

* cited by examiner

GENE DETECTING CHIP, DETECTOR, AND DETECTING METHOD

TECHNICAL FIELD

This invention relates to a gene detecting chip, detection apparatus, and detection method capable of detecting and analyzing genetic abnormalities such as DNA single base substitution SNP (single nucleotide polymorphism: variety in human genetic code), plural base substitution, point mutation, and genetic loss, etc., as well as addition of base sequences in genes.

BACKGROUND ART

Single base substitution SNP refers to a single base change in the base sequence in human DNA said to occur once in from 1000 bp to 2000 bp. It is estimated that adult humans, whether healthy or sick, have from 100,000 to several million SNPs.

Plural base substitution refers to a change in a number of bases in the base sequence of a gene.

Point mutation refers to a single-base change in the base sequence in an already known gene. It is by this that functional anomalies in translated protein are seen, and [this] sometimes becomes a cause of disease.

Gene translocation refers to the partial reversal of the order in a base sequence, which sometimes becomes a cause of disease.

Gene loss refers to a partial deficiency in a base sequence, which sometimes becomes a cause of disease.

Gene amplification refers to the multiplication of a portion of a base sequence, which sometimes becomes a cause of disease.

Triplet repeat refers to three base pairs repeating and growing, which sometimes becomes a cause of disease.

Means for detecting and analyzing differences in the base sequences in genetic DNA include DNA sequencing (base sequence determination method), the PCR-SSCP (polymerase chain reaction—single stranded polymorphism) method, the allele-specific hybridization method, the DNA chip method, and etc.

In DNA sequencing, there is the Maxam-Gilbert method and the Sanger (dideoxy) method, with the latter being principally used today. After amplifying the region of the human gene to be analyzed by the PCR (polymerase chain reaction) method, sequencing is performed using either the primer used in the PCR method or a primer set inside the amplified DNA, and the nucleotide sequence inside that region is determined.

With the PCR-SSCP (polymerase chain reaction—single stranded polymorphism) method, after using the PCR method to amplify the region of the human gene to be analyzed, this is made into single strand by thermal denaturation, and, by performing electrophoresis thereon in a non-denaturing polyacrylamide gel, a two-dimensional structure is formed (by intramolecular hydrogen bonds) in each strand of the two-strand DNA amplified by the PCR method. Because the two-dimensional structures will differ due to differences in the sequences, single base substitution SNPs and point mutations and the like are detected by differences in electrophoretic distance.

With the allele-specific hybridization method, oligonucleotide probes or PCR products of 20 bases or so are immobilized to a region of a membrane (nylon filter), and after amplifying the region to be analyzed by the PCR method, this sample DNA is labeled with the radioactive isotope 32P and hybridized. By adjusting the hybridization conditions such as temperature and the like at this time, SNPs and point mutations are detected by differences in the strength of the radioactive isotope.

With the DNA chip method, although in principle this is roughly the same as the allele-specific hybridization method, the oligonucleotide probes or PCR products for 20 bases or so are aligned in a stationary phase (on a substrate), and there the fluorescence labeled sample DNA is hybridized. By adjusting the hybridization conditions such as temperature and the like, the SNPs and the like in human genes are detected by differences in the intensity of fluorescence.

In the case of hybridization in the allele-specific hybridization method, because DNA is labeled with a radioactive isotope, the enormous cost involved in handling and controlling the radioactive isotopes becomes a problem. In the case of the DNA chip method, when labeling is done with a fluorescent radical, fluorescence is not incorporated into the DNA with adequate frequency due to the large molecular structure of the fluorescent radical, wherefore the fluorescent strength of the fluorescence labeled probe is not high, and other problems are encountered, namely fluorescence fading and the fluorescence exhibited by the glass or other platform (background fluorescence).

In order to resolve problems as these, as methods for detecting DNA hybrid formation and detecting two-strand DNA that are simple but exhibit outstanding sensitivity, methods have been disclosed wherewith the probe DNA is fixed to an electrode, that probe DNA is caused to react with sample DNA, two-strand DNA is detected in the presence of an intercalator, and the detection of the hybrid formation is performed electrochemically (cf. Japanese Patent Application Laid-Open No. H9-288080/1997 (published) and *Dai57kai bunseki kagaku toronkai yokoshu* [57th *analytical chemistry debate manuscript collection*], pp 137 and 138, 1996).

However, the number of gene single base substitution SNPs and gene mutations and the like are enormous. In the case of humans, for example, in order to produce a single base substitution SNP map with a 15 KB density (resolution), at least 2 million single base substitution SNPs must be identified. The number of gene mutations involved in known diseases is also extremely large. It is virtually impossible, realistically, to comprehensively analyze single base substitutions and point mutations with the conventional methods.

An object of the present invention is to resolve the problems with the prior art noted in the foregoing. To that end, the present invention provides a gene identification apparatus capable of detecting and analyzing large volumes of genes, for a plurality of sample DNA, that is, a gene identification apparatus capable of high throughput (fast and high volume) processing, and also capable of performing high-sensitivity detection and analysis. In fine, the present invention seeks to realize a high-volume, high-sensitivity gene detection and analysis apparatus that is based on the principle of electrochemically performing two-strand DNA detection and hybrid formation detection described in Japanese Patent Application Laid-Open No. H9-288080/1997 (published).

The present invention also seeks to realize a gene detection method, detection apparatus, and detecting chip that, in actual operations involving detection and the like, feature ease of handling and good workability.

DISCLOSURE OF THE INVENTION

The present invention provides a gene detecting chip characterized in that the chip has a plurality of pin electrodes that are measurement poles, in that a voltage is applied between the pin electrodes and a common electrode that is a counter electrode to the pin electrodes, and in that it is capable of detecting electric currents.

With the present invention, because a plurality of pin electrodes arranged in an array is used, a large volume of genes can be analyzed simultaneously.

There are also advantages in that genes can be immobilized to the pin tip parts and side surface parts, and that the area for immobilization can be made large.

There is another advantage in that, compared to cases where genes are dispensed on a flat electrode, wherewith uniform immobilization cannot be done when the surface of the flat electrode is uneven, immobilization is performed by inserting the pin electrodes into a solution containing the genes, so that certain volumes of genes can be immobilized evenly even when the surfaces of the pin electrodes are uneven. By being able to immobilize a certain volume of genes, precision and sensitivity are enhanced in quantitative analysis.

Furthermore, with the present invention, there is no need for an operation to dispense the liquid containing the genes, simplifying the operation.

With the present invention, after detection has been done by hybridization between sample DNA and probe genes immobilized to the pin electrodes, the sample DNA can be removed, and a different sample DNA can then be hybridized, allowing the chip to be used over and over. Alternatively, a process for removing the probe genes can be performed, and different probe genes are then immobilized to the pin electrodes, allowing the chip to be used repeatedly in different detection applications The detecting chip in the present invention may also have a common electrode deployed so that it is a counter electrode to the pin electrodes but does not contact those pin electrodes.

The detecting chip in the present invention may have a recess therein capable of accepting the pins and capable of being filled with sample DNA.

It is also permissible for genes having different nucleotide sequences to be immobilized to the pin electrodes.

A plurality of PCR products, oligonucleotides, mRNA, cDNA, PNA (peptidic nucleic acid), or LNA (locked nucleic acid), having a different nucleotide sequence may also be immobilized to the pin electrodes.

Another detecting chip relating to the present invention may have genes having the same nucleotide sequences immobilized respectively to the pin electrodes.

PCR products, oligonucleotides, mRNA, cDNA, PNA (peptidic nucleic acid), or LNA (locked nucleic acid; Proglio, trademark of LLC) may also be immobilized to the pin electrodes.

This detecting chip may be made so that it has a plurality of recesses capable of accepting the pin electrodes and of being filled with sample DNA, so that the plurality of recesses can be filled, respectively, with different sample DNA.

The gene detecting chips described in the foregoing are useful for detecting base sequences in genes, single base substitution SNPs, plural base substitutions, point mutations, translocations, losses, amplifications, and triplet repeats, for example.

The surfaces of the pin electrodes may be plated with gold.

The surfaces of the pin electrodes may be partially coated with a resin.

That resin may be a PEEK (polyether ether ketone) or PTFE (polytetrafluoroethylene).

The gene detecting chips described in the foregoing may be made so as to have a supporting member for supporting the pin electrodes, and to have the pin electrodes erected in that supporting member.

Here, "erected" is meant that the pin electrodes are deployed with the supporting member at the foundation such that they protrude from the supporting member.

The pin electrodes may be erected on the supporting member through spot electrodes.

"Spot electrode" is an electrode that is deployed on a spot on a supporting member.

The gene detecting chips may be made so that they also have a supporting member for supporting the pin electrodes, with one end of [each of] the pin electrodes implanted in that supporting member.

Here, "Implanting" is meant that one end of a pin electrode is fit into a concavity provided in the supporting member, and the pin electrode is deployed so that it protrudes from the supporting member.

The supporting member noted above may be a circuit board.

The pin electrodes may be fixed onto the supporting member with the ends that contact or are implanted in the supporting member enclosed in an epoxy resin or PTFE.

In the pin electrodes, genes may be immobilized only to the ends on the opposite end from the ends contacting or implanted on the supporting member, or, alternatively, genes may be immobilized to all of the pin electrodes.

A provision may also be made so that, by implementing resin coating in prescribed locations on the surfaces of the pin electrodes, genes are fixed only to the parts that are exposed without being coated.

The gene detecting chip may have a gap in the interior thereof, with the pin electrodes deployed on the supporting member so that they protrude into that gap, with a portion or the entirety of the common electrode exposed inside that gap.

The chip may be provided with an injection port that communicates to the inside of the gap, so that sample genes and electrolyte and the like can be injected into and evacuated from the interior of that gap.

The gene detecting chip may have a main body part and a frame part capable of coupling with that main body part, with the main body part having the pin electrodes on the inside surface thereof, and the frame part having a recess on the inner surface thereof capable of accepting the pin electrodes and of being filled with sample DNA when coupled with the main body part.

The main body part and the frame part may be freely attachable and detachable.

For a configuration that couples the main body part and the frame part so that they are freely attachable and detachable, a known method may be suitably employed, such as a configuration wherein a convex part or parts are provided in one of either the main body part or frame part, a concave part or parts are provided in the other part, and those convex and concave parts are engaged. Another configuration is to fasten the two [members] with clips or clamps. Further configurations are to fit one to the other by sliding, or to draw both together by a magnet, etc.

In order to resolve the problems noted earlier, the present invention provides a chip for detecting single base substitution SNPs and point mutations in genes having a main body part and a frame part that are mutually attachable and detachable, the main body part whereof has a plurality of pin electrodes that are measurement electrodes that are arranged and made to protrude in a matrix on the inner surface thereof, the frame part whereof has a recess in the inner surface thereof that can accept the plurality of pin electrodes and can be filled with sample DNA when the main body part is mounted, having a common electrode that is a counter electrode deployed in the recess so that it does not contact the pin electrodes, the pin electrodes have oligonucleotides or PCR products made up of different nucleotide sequences immobilized thereto, wherewith it is possible to have a voltage applied across the common electrode and the pin electrodes and to detect currents.

Moreover, "matrix pattern" in the present invention, is meant to be a condition wherein multiple pin electrodes are deployed so that they protrude from a prescribed surface and so that they are mutually parallel.

The pin electrodes may be plurally arranged in individual matrix patterns, such that, by inserting them, individually, into receptacles for accommodating oligonucleotides or PCR products consisting of different nucleotide sequences, the oligonucleotides or PCR products consisting of different nucleotide sequences are immobilized.

The detecting chip may be for genetic diagnostics. By performing genetic diagnostics, it is possible to examine so as to determine whether or not the patient possess genes related to single gene diseases such as muscular dystrophy, hemophilia, or phenyl ketone urinary disease, etc., or to multiple factor genetic diseases as sugar diabetes, cancer, high blood pressure, myocardial infarction, and obesity, etc., to diagnose genes prior to the onset of disease, and to obtain decision-making materials for selecting suitable treatment methods and drugs.

In order to resolve the problems noted earlier, the present invention moreover provides a gene detecting chip, and a gene detection apparatus having a measurement apparatus capable of having that detecting chip loaded therein and unloaded therefrom.

In this detecting apparatus, a Peltier element may be used, as temperature control means, to make the temperature controllable.

In order to resolve the problems noted earlier, the present invention still further provides a detection method that uses the gene detecting chip noted earlier, which is a detection method wherewith the interior of the recess is loaded with sample DNA or DNA that has been gene-amplified from sample DNA, hybridization is performed and a double-strand nucleic acid is formed, after which the remaining sample DNA or the DNA gene-amplified from sample DNA is removed from the recess and washed, after which the interior of the recess is filled with an electrolyte containing electrochemically active molecules, the electrochemically active molecules are bonded to the double-strand, a voltage is applied across the common electrode and the pin electrodes, and the values of the currents that flow are detected.

Alternatively, a detection method is provided that uses the gene detecting chip noted earlier, wherewith the interior of the recess is filled with sample DNA or DNA gene-amplified from sample DNA, together with electrolyte containing electrochemically active molecules, hybridization is performed and, while forming the double-strand, the electrochemically active molecules are bonded to the double-strand, a voltage is applied across the common electrode and the pin electrodes, and the values of the currents that flow are detected.

It is thus possible to analyze a large volume of genes simultaneously, with extremely high precision and high sensitivity, in an extremely simple operation, by causing electrochemically active molecules to bond after hybridization, or, alternately, by performing hybridization in the presence of electrochemically active molecules, using the chip described earlier.

In the detection method described earlier, a provision may be made so that the electrochemically active molecules are bonded to the double-strand while controlling the temperature.

The electrolyte containing the electrochemically active molecule may be an electrolyte having ferrocene, catecholamine, metal bipyridine complex, metal phenanthrene complex, viologen, or a threading intercalator that has-inducted those compounds as its effective component. The ferrocene threading intercalator is particularly desirable.

For the electrolyte containing the electrochemically active molecules, in addition to those [electrolytes] noted above, [those] having ethidium, ethidium bromide, acridine, aminoacridine, acridine orange, proflavine, ellipticine, actinomycin D, donomycin, mitomycin, tris(phenanthroline) zinc complex, tris(phenanthroline) ruthenium complex, tris (phenanthroline) cobalt complex, di(phenanthroline) zinc complex, di(phenanthroline) ruthenium complex, di(phenanthroline) cobalt complex, bipyridine platinum complex, terpyridine platinum complex, phenanthroline platinum complex, tris(pyridyl) cobalt complex, di(bipyridyl) zinc complex, di(bipyridyl) ruthenium complex, or di(bipyridyl) cobalt complex as the effective component are permissible.

BRIEF DESCRIPTION OF THE DRAWINGS

FIG. 3(a) is the A—A section of [the chip diagrammed in] FIG. 2(c), FIG. 3(b) is an enlarged view of the main parts of [the chip diagrammed in] FIG. 3(a), and FIG. 3(c)–3(e) are diagrams of various configurations for deploying pin electrodes on a circuit board;

BEST MODE FOR CARRYING OUT THE INVENTION

Aspects of the gene detection method, detection apparatus, and detecting chip relating to the present invention are described below with reference to the drawings. The drawings represent nothing more than one embodiment of the present invention, and [the invention] is not limited thereto or thereby.

Figure 1:
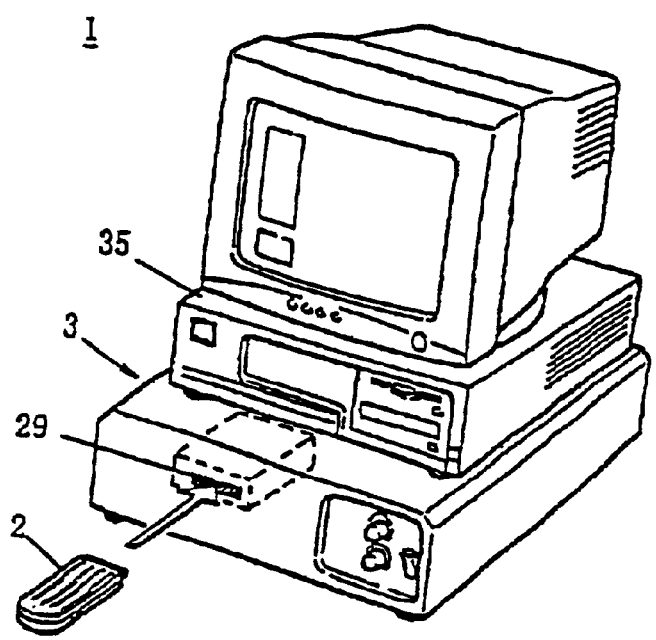
FIG. 1 is a diagonal view for describing the overall configuration of a gene detection apparatus relating to the present invention.

In FIG. 1, a gene detection apparatus 1 relating to the present invention is configured by a measurement apparatus 3 that has a detecting chip 2 and a loading slot 29 into which the detecting chip 2 can be plugged, that is capable of detecting and analyzing two-strand DNA produced by hybridization, and a personal computer 35.

Figure 2:
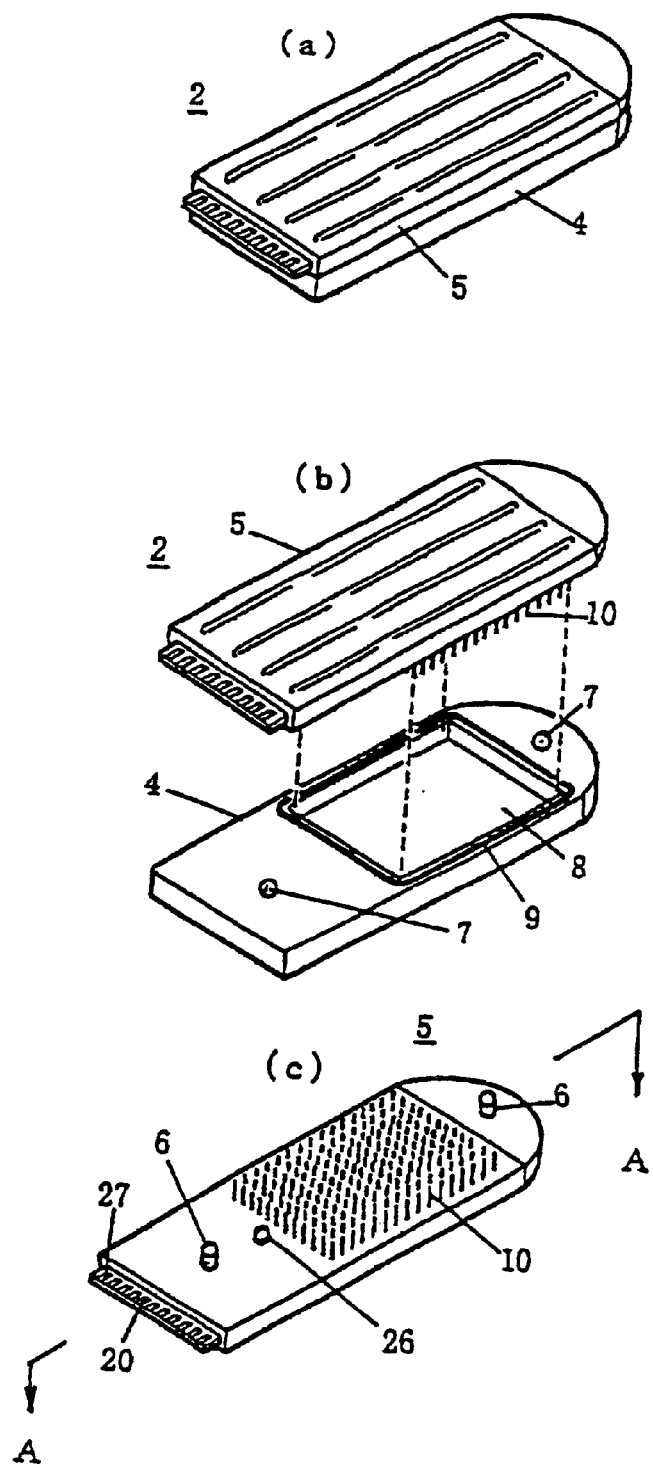
FIGS. 2a-c a diagonal view for describing the overall configuration of a gene detecting chip relating to the present invention.

FIG. 2 is a diagram representing the configuration of the detecting chip 2. FIG. 2(a) provides an overall diagonal view of the detecting chip 2, which is formed in the shape of a card or cassette. As diagrammed in the exploded diagonal view given in FIG. 2(b), the detecting chip 2 is configured by a frame 4 formed of a ceramic or synthetic resin material or the like, and a main body part 5 mounted on the frame 4 so that it can be attached and detached.

The configuration for coupling the main body unit 5 to the frame 4 so that it can be freely attached and detached can be effected by, for example, forming a concavity and convexity that elastically mates together at the contacting surfaces, respectively, of the frame 4 and main body unit 5. In this example, as diagrammed in FIGS. 2(b), 2(c), 3(a), and 5(a), the attaching and detaching capability is effected by providing convex parts 6 and concave parts 7 in locations that avoid the pin electrode arrangement in the main body unit 5 and frame 4.

For the configuration for coupling the frame 4 and main body unit 5 together so that they can be freely attached and detached, a known method may be suitably adopted that fastens the two members together by clips or clamps, or causes them to be drawn together by a magnet, etc.

A rectangular recess 8 is formed roughly in the middle of the frame 4. A seal 9 is deployed about the periphery of this recess 8. This recess 8 is capable of being filled by a solution (sample DNA, threading intercalator, washing solution, etc.), and is sealed by mounting the main body unit 5 to the frame 4. By removing the main body unit 5 from the frame 4, the solution inside the recess 8 can quickly be replaced or mixed, or [the interior of the recess 8] washed.

On the other hand, in the main body unit 5 as shown in FIG. 2(c), in a region corresponding to the recess 8 of the frame 4, many pin electrodes 10 are erected uniformly. The protruding length of these pin electrodes 10 is a length that is accommodated inside the recess 8 when the main body unit 5 is mounted on the frame 4.

Figure 3:
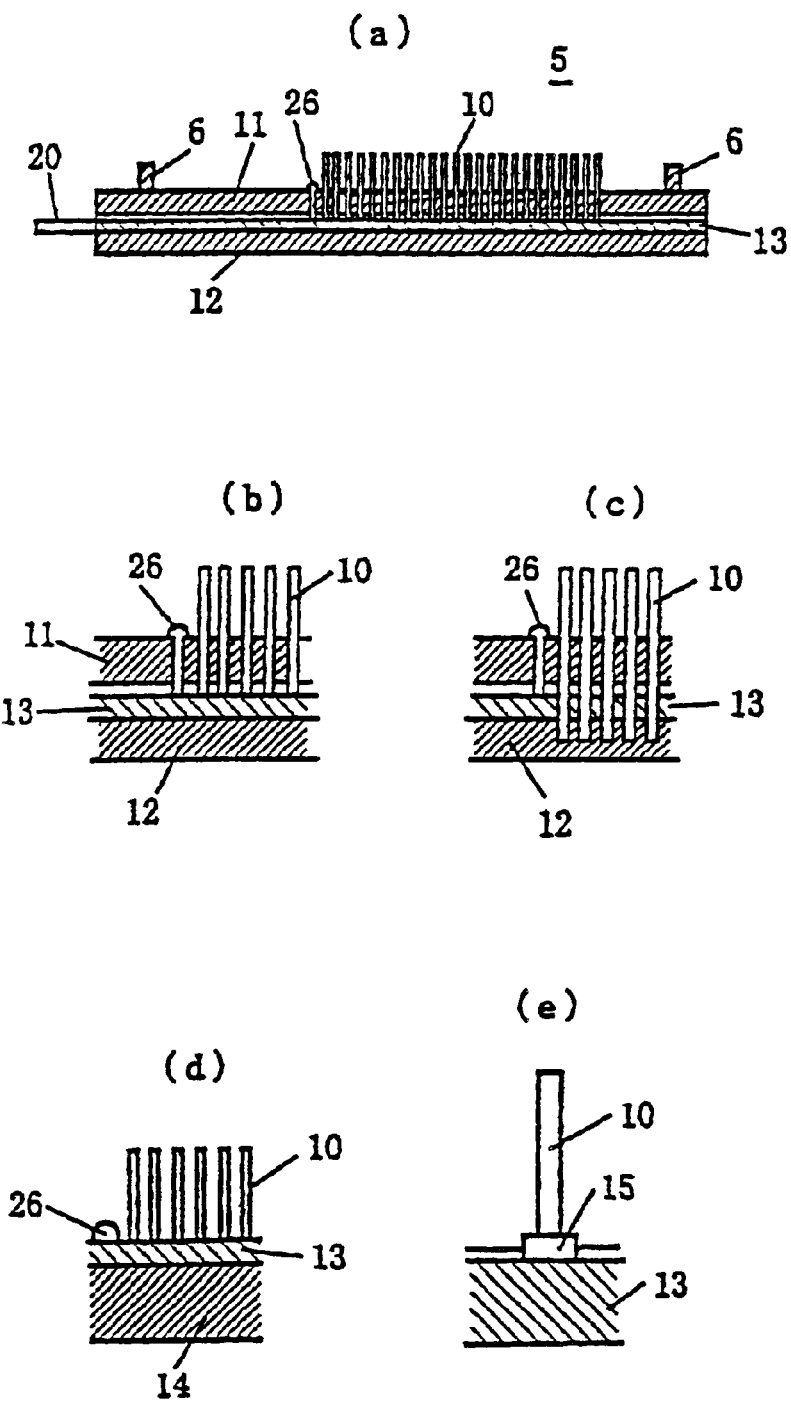

FIG. 3(a) shows the A—A section of [the main body unit 5 diagrammed in] FIG. 2(c), which represents the configuration of the main body unit 5 and the condition wherein the pin electrodes 10 are erected. The main body unit 5 is configured with a circuit board 13 provided between the inner wall 11 and outer wall 12 thereof. The end of the circuit board 13 is exposed, and terminals 20 for the pin electrodes and a terminal (designated by 27 in FIG. 4) for the common electrode are provided in that exposed portion. And in the circuit board 13 circuitry inclusive of interconnecting lines is formed (indicated by 21, 22, and 23 in FIG. 4), etc.

As diagrammed in FIGS. 3(a) and 3(b), the pin electrodes 10 are configured so that they pass from the circuit board 13 through the inner wall 11 and protrude.

The pin electrodes 10, as diagrammed in FIG. 3(c), may also be configured so that they pass from the outer wall 12 through the circuit board 13 and the inner wall 11 and protrude.

The pin electrodes 10, as diagrammed in FIG. 3(d), may also be configured so that, with the main body unit 5 [configured so that] the circuit board 13 is deployed on a base 14, the pin electrodes 10 are erected on top thereof.

Alternatively, as diagrammed in FIG. 3(e), many spot electrodes 15 may be vapor-deposited onto the circuit board 13 beforehand in order to form many spot electrodes 15, and the pin electrodes 10 erected on those spot electrodes 15 such that they are in electrical contact therewith.

As diagrammed in the enlarged view given thereof in FIG. 6(b), PCR product, SH-ized oligonucleotides 16 wherein thiol (SH) groups have been introduced to the 5' end of the oligonucleotides, are immobilized to the surfaces of the pin electrodes 10. The PCR product is a double-strand DNA, but one of the strands wherewith an SH group has been introduced to the 5' end, have a length that includes 20 to 50 bases, and is immobilized onto the pin electrodes 10 through the thiol group introduced to the base end thereof.

As diagrammed in FIG. 6(a), by inserting the pin electrodes 10 into receptacles 18 in a microplate 17 having DNA receptacles 18 arranged in the same pitch as the pin electrodes 10, it is possible to simultaneously immobilize DNA of different types. The surfaces of the pin electrodes 10 are plated with gold, and the procedure for fixing the SH-ized oligonucleotides 16 through the SH group to the gold is commonly known.

SH-gold bonding and preprocessing methods performed prior to immobilization of the oligonucleotides on the surfaces of the gold pin electrodes are described by C. D. Bain in J. Am. Chem. Soc. No. 111, pp 321 and following, 1989, and by J. J. Gooding in Anal. Chem. No. 70, pp 2396 and following, 1998. The removal of probe genes is performed by a method such as that described by C. D. Bain in J. Am. Chem. Soc. No. 111, pp 321 and following, 1989.

The multiple pin electrodes 10 are deployed on the circuit board 13, and configured such that, electrically, they form part of the circuit board. Also, as diagrammed in FIG. 2(c), the terminals 20 and 27 are deployed in parallel in the forward end part of the main body unit 5.

As diagrammed in FIGS. 4(a), 3(a), and 3(b), the pin electrodes 10 are respectively connected to the interconnecting lines 21 on the circuit board, while the other ends of those interconnecting lines 21 are connected independently to the respective terminals 20.

Figure 4:
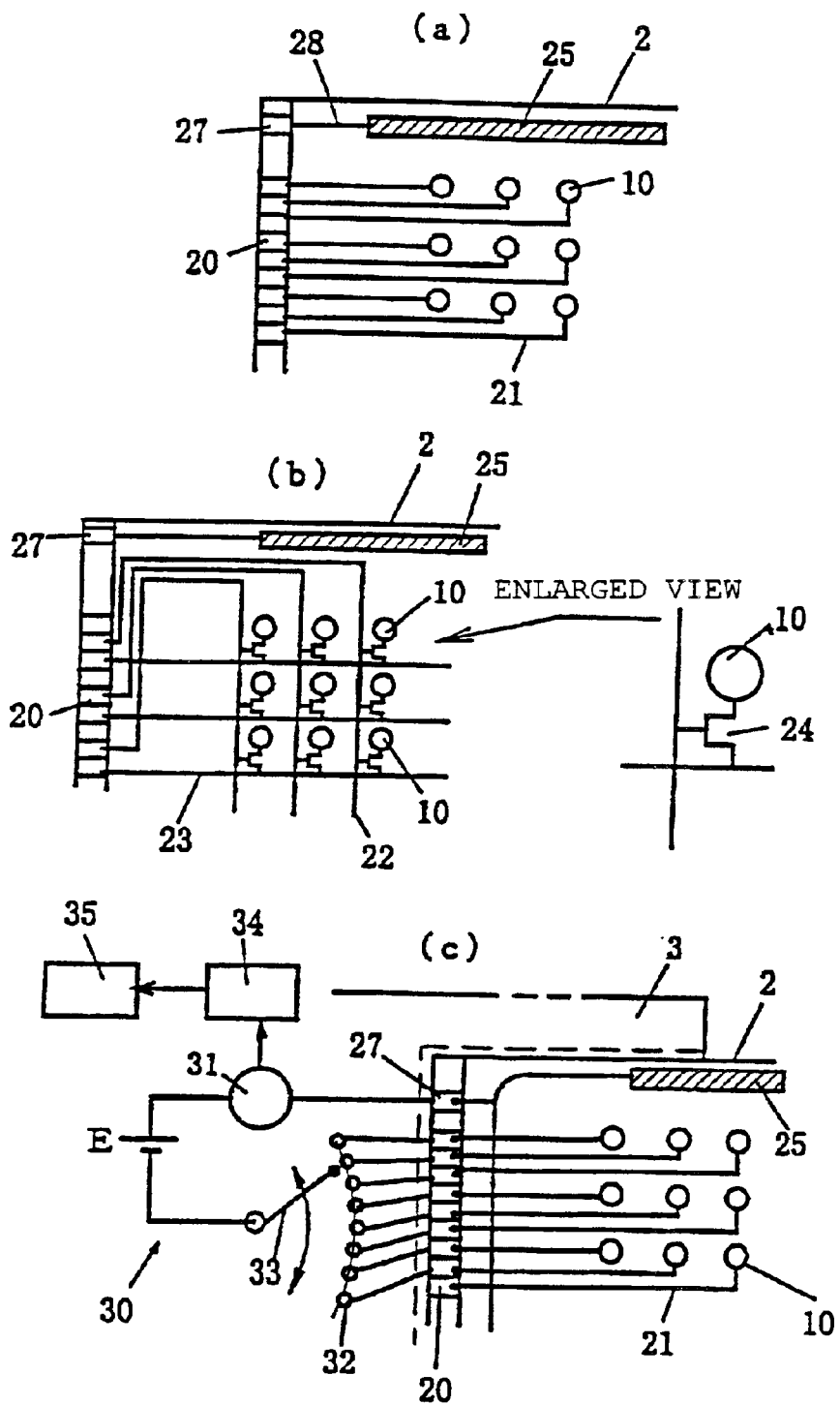
FIGS. 4a-c provides diagrams for describing the configuration of electrodes and interconnecting lines in a gene detection apparatus and detecting chip relating to the present invention.
Figure 5:
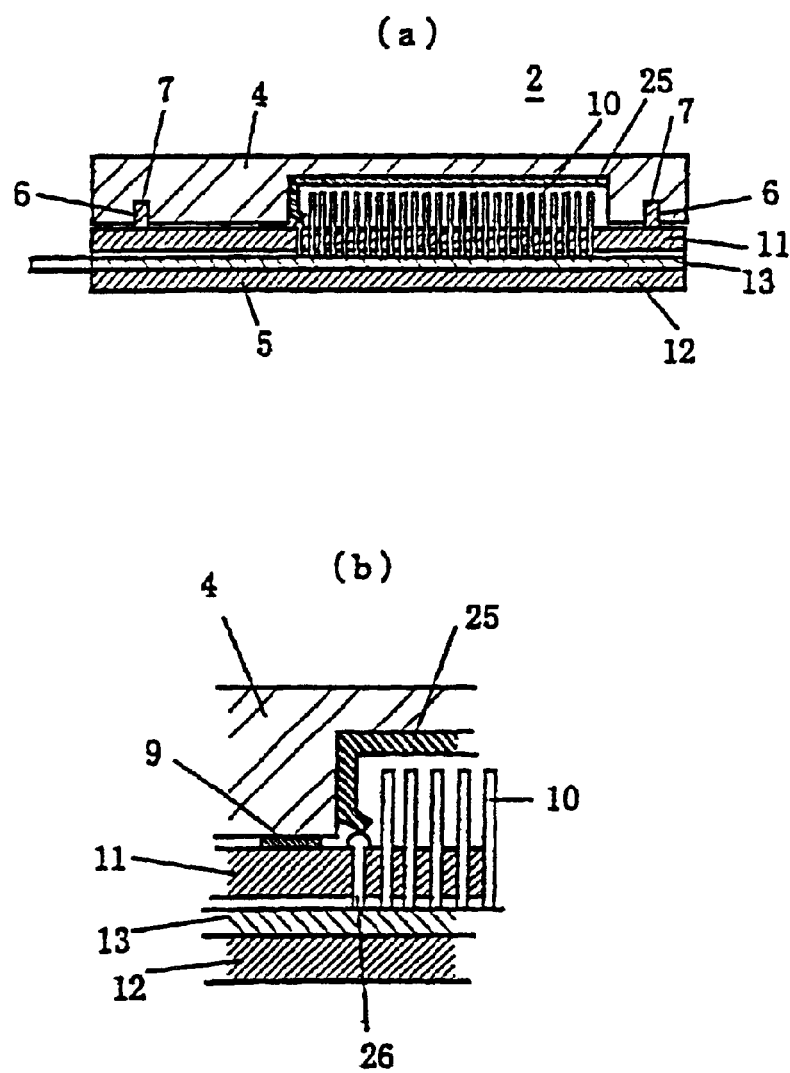
FIGS. 5a-c provides a cross-sectional view and enlarged view of the main parts of the detecting chip diagrammed in FIG. 2.

FIG. 4 diagrams a gene electrical detection circuit. As diagrammed in FIG. 4(a), the interconnecting lines 21 for the pin electrodes 10 may be connected one by one, correspondingly, to the pin electrodes 10, respectively, and connected, respectively, to the terminals 20. However, the configuration may also be made such that, as diagrammed in FIG. 4(b), the pin electrodes 10 are connected individually to matrix interconnecting line leads 22 and 23 through FETs (field effect transistors) 24 at the intersections of matrix interconnecting lines comprising multiple vertical and horizontal leads 22 and 23, as in a matrix electrode such as an active matrix type TFT liquid crystal display device wherein switching elements comprising TFTs are provided. When the configuration is made in that way, the vertical and horizontal leads 22 and 23 are scanned, selected TFTs are turned on, and specific pin electrodes are electrically connected to the terminals.

In this example, there is a common electrode 25 diagrammed in FIG. 4. The common electrode indicated in FIG. 4 is simply represented in model form for the purpose of describing the circuit configuration and, in actuality, should be deployed in the recess 8. The common electrode 25, for example, is deployed, as diagrammed in FIG. 5(a), on a portion (such as the periphery, etc.), or on the entire surface, of the bottom surface of the recess 8, or, alternatively, on the inner circumferential side surface or the like near the bottom surface of the recess 8, as a counter electrode to the pin electrodes 10. Also, the common electrode 25 is deployed in a position where it does not contact the pin electrodes 10. The common electrode 25 is configured so that, when the main body unit 5 is mounted to the frame 4, contact is made with the terminal 26 for the common electrode of the main body unit 5, as diagrammed in the enlarged view in FIG. 5(*b*). The terminal 26 for this common electrode is connected via an interconnecting line 28 to the terminal 27 for the common electrode.

The configuration may also be such that values of the currents between the respective pin electrodes 10 and the common electrode 25 that is the counter electrode are measured with reference to a reference electrode (not shown) wired so as to make contact with an electrolyte solution (described subsequently) when that electrolyte solution is filled into the space inside the recess 8, so that accurate current values are obtained with each measurement.

In the interior of the detecting chip loading slot (item 29 in FIG. 1) in the measurement apparatus, as diagrammed in FIG. 4(*c*), a circuit 30 is deployed for connecting the terminal 27 for the common electrode and the terminals 20 for the pin electrodes, and applying voltages between the terminal 27 for the common electrode and the terminals 20 for the pin electrodes.

The configuration is made such that, when a voltage E is applied across the terminal 27 for the common electrode and the terminals 20 for the pin electrodes, the currents that flow between the common electrode 25 and the pin electrodes 10 can be detected and measured by a detector 31 deployed in the circuit 30.

Furthermore, in order to selectively connect the terminals 20 of the pin electrodes 10, the measurement apparatus 3 is provided with receiving terminals 32 which are connected to the terminals 20 for the pin electrodes when the detecting chip 2 is plugged in through the loading slot 29, and with a scanning terminal 33 for selectively connecting the receiving terminals 32 to the circuit 30.

The measurement data based on these detected currents are digitized by an A–D converter 34 connecting to the detector 31, and used as processing data by the personal computer 35 for analyzing and identifying and otherwise processing the sample DNA.

Moreover, the measurement apparatus 3 is equipped with a temperature controller (not shown) having a Peltier element. The temperature conditions of the hybridization described subsequently can be controlled by this temperature controller.

Figure 6:
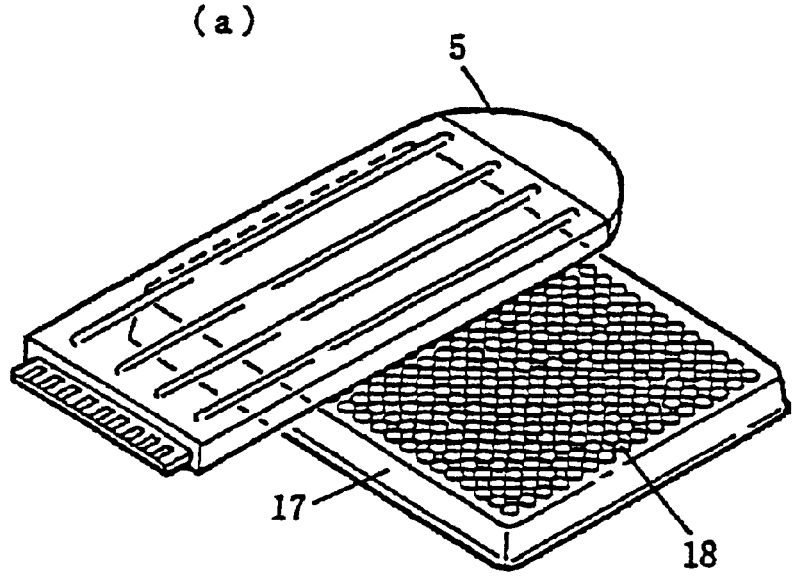
FIGS. 6a-b provides diagonal views for describing how a gene detecting chip relating to the present invention is used.
Figure 6:
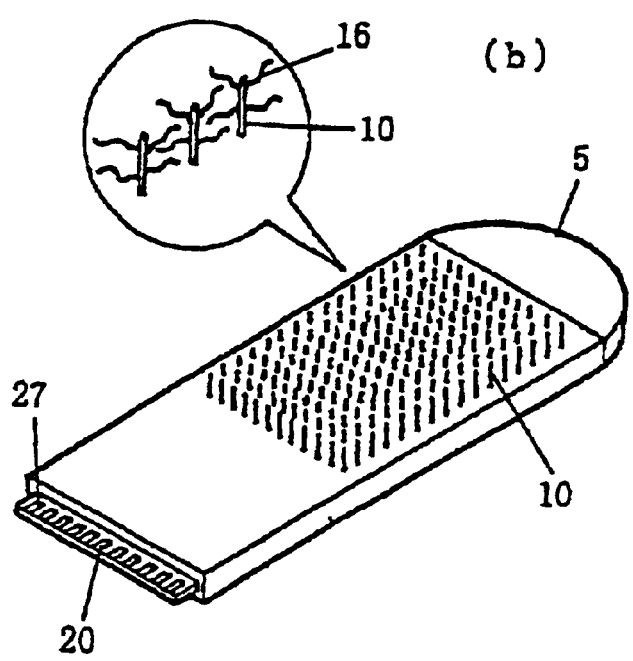

The operation of the detection apparatus 1 relating to the present invention and comprising the configuration described in the foregoing will now be described. In FIG. 6(*a*) shows a microplate where on receptacles 18 are arranged in an array with the same pitch as the pin electrodes 10. Inside the receptacles 18 of this microplate 17, DNA of the same or different types are accommodated.

As diagrammed in FIG. 6(*a*), the multiple pin electrodes 10 in the main body unit 5 of the detecting chip 2 are inserted respectively into the receptacles 18. Thus, as diagrammed in the partial enlarged view thereof in FIG. 6(*b*), DNA of the same or differing types can be immobilized on the pin electrodes 10.

Meanwhile, sample DNA solution is injected to fill the interior of the recess 8 in the frame 4. Then, the main body unit 5 is mounted to the frame 4, engaging the convex parts and concave parts, so that the multiple pin electrodes 10 adorned by the DNA are inserted into the recess 8. Thereupon, the interior of the recess 8 is sealed by the seal 9, and the common electrode 25 makes contact with the terminal 26 for the common electrode of the main body unit 5.

For the sample DNA, DNA extracted from biological material that has been processed with a DNA cleavage enzyme or ultrasonic process, or DNA amplified by PCR (polymerase chain reaction method) from specific genes is used. These sample DNAs are denatured ahead of time by heat treatment immediately prior to hybridization.

When the sample DNA (in a single strand state) is added to the PCR product or oligonucleotide DNA (in a single strand state) immobilized to the pin electrodes, hybridization is effected with the sample DNA and the oligonucleotide DNA or PCR product having mutually complementary base sequences.

During this hybridization, the detecting chip 2 is plugged into the loading slot 29 and loaded into the measurement apparatus 3, and the temperature conditions of the hybridization are controlled by the temperature controller having the Peltier element provided inside the measurement apparatus 3.

After this hybridization has been completed, the detecting chip 2 is pulled out of the measurement apparatus 3, and the main body unit 5 is removed from the frame 4. The sample DNA solution is removed from the interior of the recess 8, the interior of the recess 8 is flushed with washing liquid, and washing, which washes away the unhybridized sample DNA, is done.

After this washing, the interior of the recess 8 is filled with an electrolyte solution containing electrochemically active molecules and the main body unit 5 is mounted on the frame 4. The electrochemically active molecules exhibit the function of changing the resistance value and other electrical properties of the double-strand DNA produced by hybridization. This point is explained in detail in Japanese Patent Application Laid-Open No. H9-288080/1997 (published).

The detecting chip 2 on which such processing has been done is reloaded into the measurement apparatus 3, the terminal 27 for the common electrode and the terminals 20 for the pin electrodes of the detecting chip 2 are connected to the receiving terminals 32 of the measurement apparatus, connected to a voltage circuit 30 through a selector switch, and a weak voltage is applied across the common electrode 25 and the pin electrodes 10, whereupon a very weak current flows through the voltage circuit 30 and the common electrode 25 to the pin electrodes 10 connected to the double-strand DNA produced by hybridization. The temperature is controlled by the Peltier element mounted inside the measurement apparatus 3, and current values are measured at different temperatures.

In the measurement apparatus 3, as diagrammed in FIG. 4(*c*), the scanning element 33 is switched relative to the terminals 20 for the pin electrodes and the receiving terminals 32 (It being possible to perform that switching either automatically or manually. Further description whereof is omitted here, however, because the configuration thereof is not important to this description), whereby currents flow sequentially to the double-strand DNA after hybridization, which are detected by the detector 31.

These detection results are converted to digital data by the A–D converter 34, and stored in a memory or the like as measurement data by the personal computer 35. Sample DNA is identified and analyzed according to those measurement data. By comparing [those data] with various types of pre-stored DNA data and the like, for example, it is possible to analyze and identify sample DNA.

Examples of experiments of a gene electrochemical detection apparatus relating to the present invention will now be described.

EXPERIMENTAL EXAMPLE 1

An experimental example for the detection of a single-base substitution SNP in the 72nd codon of the gene p53 is represented. Oligonucleotides having base sequences corresponding to the two types of polymorphism (genetic polymorphism) were immobilized by spotting respectively to the pin electrodes 10.

p53Pro (72nd codon whereof is Pro)

p53Arg (72nd codon whereof is Arg)

To this, DNA was taken from the peripheral blood of a healthy human wherein the 72nd codon of p53 is Pro and PCR amplified product, wherein the region containing codon 72 exists in the exon 4 of p53 from that DNA, was thermally denatured and then subjected to a hybridization reaction. The variation in the current value before and after hybridization at 470 mV (Ag/AgCl reference electrode standard) at 20 degrees Celsius in the measurement electrolyte solution (0.1M AcOH-AcOK (pH 5.6), 0.1M KCl, 0.05 mM NFc) was measured.

DNA taken from peripheral blood

| p53Pro current variation (%) | 52% |
| p53Arg current variation (%) | 15% |

PCR Product

| p53Pro current variation (%) | 65% |
| p53Arg current variation (%) | 13% |

Further, the DNA taken from the peripheral blood of a healthy human wherein the 72nd codon in p53 is Arg and the PCR amplified product, wherein the region containing codon 72 exists in the exon 4 of p53 from that DNA, was subjected similarly to hybridization.

DNA taken from peripheral blood

| p53Pro current variation (%) | 46% |
| p53Arg current variation (%) | 17% |

PCR Product

| p53Pro current variation (%) | 53% |
| p53Arg current variation (%) | 11% |

These current variations exhibited clear differences in cases where the base sequences matched perfectly and in cases of mismatch.

EXPERIMENTAL EXAMPLE 2

The measured current value differs depending on the number of base substitutions, and an experimental example is described that shows that the mismatch volume can be measured thereby. Seven types of oligonucleotides, namely dT20, dT10dAdT9, dT8dA4dT8, dAdT19, dA3dT17, dT19dA, and dT17dA3, were immobilized by spotting respectively to the pin electrodes 10. As the hybridization counterpart, dA20 was subjected to hybridization reaction.

The variation in the current values before and after hybridization was measured at 470 mV (Ag/AgCl reference electrode standard) at 20 degrees Celsius in the measurement electrolyte solution (0.1M AcOH-AcOK (pH 5.6), 0.1M KCl, 0.05 mM NFc).

The measurement results are indicated in Table 1

TABLE 1

Current variation (%)
Tm (degrees)

The current variation in Table 1 is roughly dependent on the number of mismatched bases. In cases where mismatches exist in the end parts, in particular, variation larger than the Tm value was observed. With conventional SSCP, such systems could not be detected; they became clear for the first time with this procedure.

EXPERIMENTAL EXAMPLE 3

An experimental example for the quantitative measurement of mRNA expression quantities is represented. That wherein a thiol group (HS) was introduced to the end of an oligonucleotide 5' of a unique sequence 40-mer existing on an LacZ gene on the E. coli lactose operon and this oligonucleotide was immobilized respectively to the pin electrodes 10 (HS-m1: 60 fmol).

Also, mRNA liquid extract from E. coli containing mRNA of a different expression levels was placed in (a) different well(s) on a titer plate. The previously prepared pin electrodes 10 were immersed into the wells of this titer plate, and a hybridization reaction was conducted under conditions of 2× SSC, room temperature, and 1 hour. [For] this, the variation in the current value before and after hybridization at 470 mV (Ag/AgCl reference electrode standard) at 20 degrees in the measurement electrolyte solution (0.1M AcOH-AcOK (pH 5.6), 0.1M KCl, 0.05 mM NFc) was measured.

Figure 7:
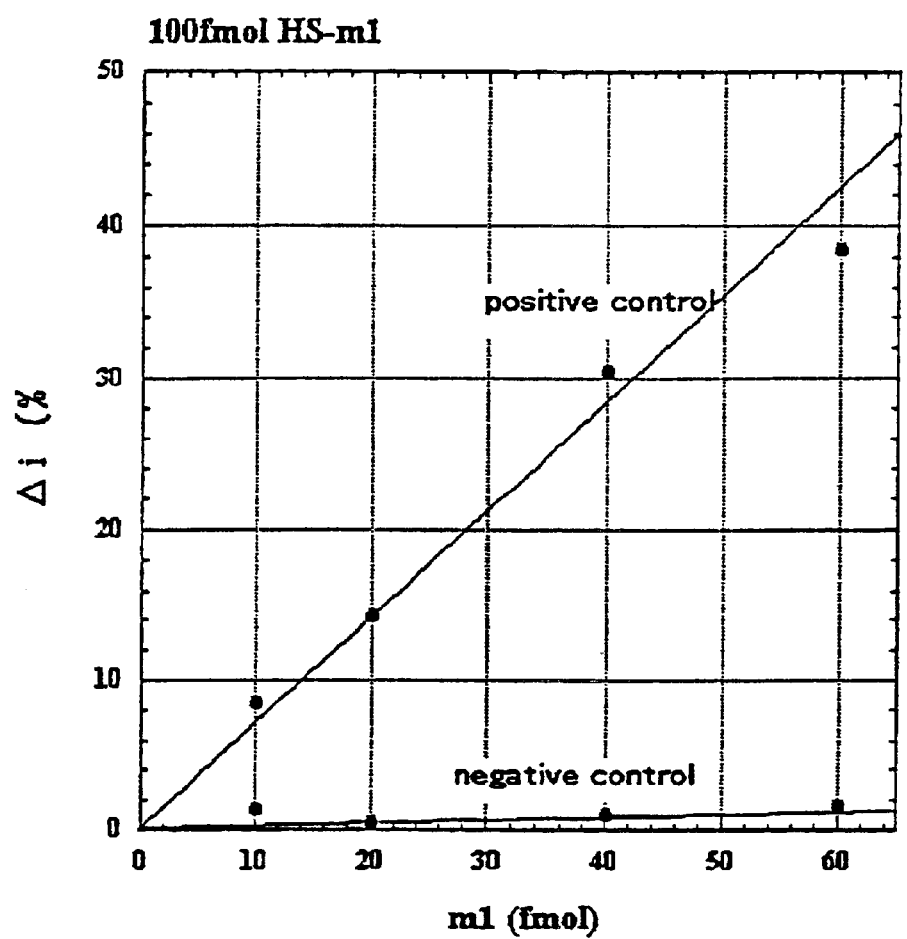
FIG. 7 is [a graphical representation of] the experimental example 3 measurement results.

The measurement results obtained are indicated in FIG. 7. As may be seen from FIG. 7, the current variation Δi (%) increased linearly in conjunction with the increase in the mRNA quantity up to an mRNA quantity of 60 fmol.

It is thus seen that, in this example, the mRNA expression amount can be quantitatively determined at the fmol level.

EXPERIMENTAL EXAMPLE 4

An experimental example concerning gene detection is represented. A DNA probe (5'-HS-AAGGTTGATTACTGGAATGGGGACCTGTTA-3') for detecting genes in cytochrome C from African clawed frog (Xenopus sp.) egg cells was fixed to the pin electrodes 10, respectively. Solutions containing the target gene (DNA complementary to probe oligonucleotide) of different DNA concentrations were placed in (a) different well(s) on the titer plate. The previously prepared pin electrodes 10 were immersed into the wells of this titer plate, and a hybridization reaction was conducted under conditions of 2× SSC, room temperature, and for 1 hour. [For] this, the variation in the current value before and after hybridization at 470 mV (Ag/AgCl reference electrode standard) at 20 degrees in the measurement electrolyte solution (0.1 M AcOH-AcOK (pH 5.6), 0.1M KCl, 0.05 mM NFc) was measured.

Figure 8:
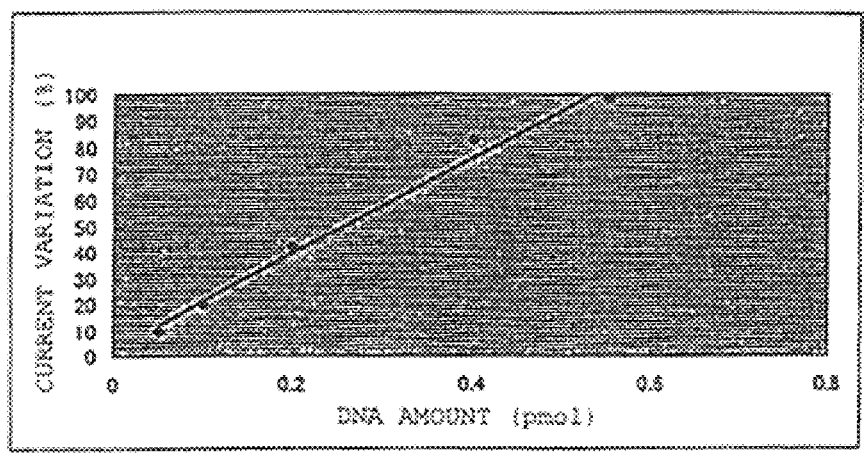
FIG. 8 is [a graphical representation of] the experimental example 4 measurement results.

The measurement results obtained are indicated in FIG. 8. As may be seen from FIG. 8, from several tens to several hundreds of fmol of the target gene could be detected. On the other hand, almost no variation in current for the DNA sample not containing the cytochrome C was observed.

The gene detection method, detection apparatus, and detecting chip relating to the present invention have been described in the foregoing in terms of examples thereof, but the present invention is not limited to or by those examples. Needless to say, there are various embodiments within the scope of the technical provisions of the claims.

INDUSTRIAL APPLICABILITY

The gene detection method, detection apparatus, and detecting chip relating to the present invention, being configured as described in the foregoing, can detect and analyze genes with high sensitivity, at high speed and high volume, simply and conveniently.

Thus the detection apparatus relating to the present invention that is capable of high-sensitivity, high-throughput (high speed, large volume) processing provides effective means for the correlative analysis of genes and expression phenotypes in the fields of biology and medicine. By analyzing drug metabolizing enzymes and specific genes such as cancer inhibitor genes using the detecting and analyzing apparatus for,gene base sequences, single base substitution SNPs, plural base substitutions, point mutations, translocations, losses, amplifications, and triplet repeats. The invention can also be used in genetic diagnosis.

With the detection apparatus relating to the present invention, for example, it is possible to effect high-sensitivity, high-throughput (high speed, large volume) processing, wherefore [that apparatus] can be used to good effect in collecting data relating to Japanese human genes, identifying genes connected with the onset of disease, and predicting and preventing future disease occurrence.

Moreover, by diagnosing genes, [the invention] can be used to good effect in selecting suitable treatment methods and selecting drugs having few side effects.

Furthermore, using the results of disease gene analysis, new drugs can be developed without repeating clinical experiments and the like.

With the present invention, a detecting chip is configured of a main body part and a frame part that can be freely attached together and detached, and a recess, formed in the frame part that can be filled with sample DNA solution or the like. Therefore solutions of sample DNA and threading intercalator and the like can be loaded and extracted by extremely simple operations, and the interior of the recess can be easily washed with a washing liquid.

With the present invention, as measurement poles in the detecting chip, pin electrodes are provided such that they are erected in a matrix arrangement inside the main body unit. Therefore, by inserting the pin electrodes into the receptacles of microplates accommodating different DNA, DNA of different types can simultaneously be immobilized at one time.

What is claimed is:

1. A gene detecting chip comprising:
    a body part having a plurality of pin electrodes on an inside surface thereof;
    a frame part having a recess on an inner surface thereof and being freely attachable to and detachable from said body part, said frame part being capable of accepting the pin electrodes and of being filled with a nucleic acid sample; and
    a common electrode being a counter electrode for the pin electrodes, wherein said common electrode is arranged within the recess in a manner that said common electrode does not come into contact with the pin electrodes.

2. The gene detecting chip according to claim 1, wherein genes having different nucleotide sequences are immobilized to said pin electrodes.

3. The gene detecting chip according to claim 1, wherein a plurality of different nucleotide sequences, selected from the group consisting of PCR products, oligonucleotides, mRNA, cDNA, peptidic nucleic acid, and a bicyclic nucleic acid wherein a ribonucleoside is linked between the 2'-oxygen and 4'-carbon atoms with a methylene unit, is immobilized to said pin electrodes.

4. The gene detecting chip according to claim 1, wherein genes having the same nucleotide sequence are immobilized to said pin electrodes.

5. The gene detecting chip according to claim 1, wherein PCR products, oligonucleotides, mRNA, cDNA, peptidic nucleic acid or a bicyclic nucleic acid wherein a ribonucleoside is linked between the 2'-oxygen and the 4'-carbon atoms with a methylene unit, having the same nucleotide sequence, are immobilized to said pin electrodes.

6. The gene detecting chip according to claims 4 or 5, further characterized by having a plurality of recesses capable of accepting said pin electrodes and capable of being filled with a nucleic acid sample, so that said plurality of recesses can be filled with different nucleic acid samples, respectively.

7. The gene detecting chip according to claim 1, wherein the chip is capable of detecting gene based sequences, one base substituted SNPs, substitution of several bases, point mutations, translocations, losses, deletions, amplifications, or triplet repeats.

8. The gene detecting chip according to claim 1, wherein the surfaces of said pin electrodes are plated with gold.

9. The gene detecting chip according to claim 1, wherein the surfaces of said pin electrodes are partially coated with a resin.

10. The gene detecting chip according to claim 9, wherein said resin is PEEK or PTFE.

11. The gene detecting chip according to claim 1, wherein a supporting member is further provided for supporting said pin electrodes, and said pin electrodes are erected on said supporting member.

12. The gene detecting chip according to claim 11, wherein said pin electrodes are erected on said supporting member with spot electrodes interposed therebetween.

13. The gene detecting chip according to claim 1, wherein a supporting member is further provided for supporting said pin electrodes, and one end of each of said pin electrodes is implanted on said supporting member.

14. The gene detecting chip according to any one of claims 11 to 13, wherein said supporting member is a circuit board.

15. The gene detecting chip according to any one of claims 11 to 13, wherein the ends of said pin electrodes, which are in contact with or implanted on said supporting member, are enclosed by an epoxy resin or PTFE and thereby secured on said supporting member.

16. The gene detecting chip according to any one of claims 11 to 13, wherein nucleotide sequences are immobilized only to ends of said pin electrodes that are not the ends in contact with or implanted on said supporting member.

17. The gene detecting chip according to claim 2, wherein genes are fixed over the entirety of said pin electrodes.

18. The gene detecting chip according to any one of claims 11,12,13 or 17 wherein a gap is formed between said body part and said frame part, said pin electrodes are deployed on said supporting member so as to protrude into said gap, and a portion or entirety of said common electrode extends into said gap.

19. A detecting chip for detecting one base substituted SNP and spot mutation in genes, comprising a main body part and a frame part that are freely attachable to and detachable from each other, characterized in that:

said main body part has a multiplicity of pin electrodes that are protruding measurement poles arranged in a matrix on the inner surface thereof;

said frame part has a recess on the inner surface thereof that is capable of accepting said multiplicity of pin electrodes when said main body part is mounted thereon and is capable of being filled with a nucleic acid sample;

a common electrode, that is a counter electrode deployed so as not to contact said pin electrodes, is provided in said recess; and PCR products or oligonucleotides having different nucleotide sequences that are immobilized to said pin electrodes, wherein voltages are applied between said common electrode and said pin electrodes so as to enable detection of currents.

20. The gene detecting chip according to claim 19, wherein said pin electrodes are arranged in a multiplicity in matrices, and, by inserting the pin electrodes into each of receptacles accommodating PCR products or oligonucleotides having different nucleotide sequences, said PCR products or oligonucleotides having different nucleotide sequences are immobilized thereto.

21. A gene detection apparatus comprising the gene detecting chip described in any one of claim 1 or 19 and a measurement apparatus which said detecting chip can be loaded into and removed from.

22. The gene detection apparatus according to claim 21, wherein said temperature of said gene detecting chip can be controlled using a Peltier element.

23. A detection method using the gene detecting chip claimed in any one of claim 2, 3, 4, 5 or 19, comprising the steps of:

filling said recess with the nucleic acid sample or a DNA gene-amplified from the sample;

performing a hybridization to form a double-strand nucleic acid between the nucleic acid sample or the DNA gene-amplified from the sample and any nucleotide sequences immobilized to the pin electrodes having mutually complementary base sequences;

removing from said recess and washing away any unhybridized nucleic acid sample or unhybridized DNA gene-amplified from the sample;

filling said recess with an electrolyte containing electrochemically active molecules such that said electrochemically active molecules are bonded to said double-strand nucleic acid;

applying voltages between said common electrode and said pin electrodes; and detecting values of currents flowing therebetween.

24. A detection method using the gene detecting chip described in any one of claim 2, 3, 4, 5 or 19, comprising the steps of:

filling said recess with the nucleic acid sample or a DNA gene-amplified from the sample and electrolyte containing electrochemically active molecules;

performing a hybridization to form double-strand nucleic acid between the nucleic acid sample or the DNA gene-amplified from the sample and any nucleotide sequences immobilized to the pin electrodes having mutually complementary base sequences, while said electrochemically active molecules are bonded to said double-strand nucleic acid;

applying voltages between said common electrode and said pin electrodes; and detecting values of currents flowing therebetween.

25. The detection method according to claim 23, wherein said electrochemically active molecules are bonded to said double-strand while controlling temperature.

26. The detection method according to claim 23, wherein said electrolyte containing said electrochemically active molecules has as its effective component, ferrocene, catecholamine, metal bipyridine complex, metal phenanthrene complex, viologen, or a threading intercalator in which those compounds are incorporated.

27. The detection method according to claim 24, wherein said electrochemically active molecules are bonded to said double-strand while controlling temperature.

28. The detection method according to claim 24, wherein said electrolyte containing said electrochemically active molecules has as its effective component, ferrocene, catecholamine, metal bipyridine complex, metal phenanthrene complex, viologen, or a threading intercalator in which those compounds are incorporated.

* * * * *